(12) United States Patent
Köhler

(10) Patent No.: US 9,937,364 B2
(45) Date of Patent: Apr. 10, 2018

(54) HIGH INTENSITY FOCUSED ULTRASOUND WITH CAPACITIVE MICROMACHINED TRANSDUCERS

(71) Applicant: KONINKLIJKE PHILIPS N.V., Eindhoven (NL)

(72) Inventor: Max Oskar Köhler, Espoo (FI)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 14/391,142

(22) PCT Filed: Apr. 9, 2013

(86) PCT No.: PCT/IB2013/052814
§ 371 (c)(1),
(2) Date: Oct. 7, 2014

(87) PCT Pub. No.: WO2013/153509
PCT Pub. Date: Oct. 17, 2013

(65) Prior Publication Data
US 2015/0065922 A1    Mar. 5, 2015

Related U.S. Application Data

(60) Provisional application No. 61/623,123, filed on Apr. 12, 2012.

(51) Int. Cl.
*A61N 7/00* (2006.01)
*A61N 7/02* (2006.01)

(52) U.S. Cl.
CPC .............. *A61N 7/00* (2013.01); *A61N 7/02* (2013.01); *A61N 2007/0004* (2013.01);
(Continued)

(58) Field of Classification Search
CPC .................................. A61N 7/02; A61N 7/00
See application file for complete search history.

(56) References Cited

U.S. PATENT DOCUMENTS 7,766,833 B2   8/2010  Lee
7,854,733 B2   12/2010 Govari
(Continued)

FOREIGN PATENT DOCUMENTS

WO   200232506 A1   4/2002
WO   2009082740 A1  7/2009
WO   2011080664 A1  7/2011

*Primary Examiner* — Hien Nguyen

(57) ABSTRACT

A medical instrument (900, 1000) comprising a high intensity focused ultrasound system (911) comprising an ultrasound transducer (102, 104, 202, 204, 302, 407, 08) with an adjustable sonication frequency. The ultrasound transducer comprises capacitive micromachined transducers (102, 104, 202, 204, 302, 407, 508). Execution of machine executable instructions by a processor causes the processor to: receive (700, 800) a treatment plan (924) descriptive of a target zone (908) within a subject (902); determine (702, 802) a traversal distance (926) through the subject to the target zone using the treatment plan, wherein the traversal distance is descriptive of the traversal of ultrasound from the ultrasound transducer to the target zone; determine (704, 804) a sonication frequency (829) using the traversal distance for focusing the sonication volume onto the target zone; and sonicate (706, 806) the target zone using the high intensity focused ultrasound system at the sonication frequency.

12 Claims, 10 Drawing Sheets

(52) U.S. Cl.
CPC .............. *A61N 2007/0043* (2013.01); *A61N 2007/0078* (2013.01); *A61N 2007/0086* (2013.01)

(56) References Cited

U.S. PATENT DOCUMENTS

| | | |
|---|---|---|
| 7,967,764 B2 | 6/2011 | Lidgren et al. |
| 8,142,358 B2 | 3/2012 | Pedrizzetti et al. |
| 8,345,513 B2 | 1/2013 | Huang |
| 8,702,609 B2 | 4/2014 | Hadjicostis |
| 2002/0082528 A1 | 6/2002 | Friedman |
| 2002/0099324 A1* | 7/2002 | Melton, Jr. .............. A61N 7/00 604/21 |
| 2008/0221448 A1 | 9/2008 | Khuri-Yakub |
| 2011/0040172 A1 | 2/2011 | Carpentier et al. |
| 2011/0144490 A1 | 6/2011 | Davis |
| 2011/0213248 A1 | 9/2011 | Murakami |
| 2011/0257523 A1 | 10/2011 | Hastings |
| 2014/0058294 A1* | 2/2014 | Gross .................... A61B 8/546 601/2 |

* cited by examiner

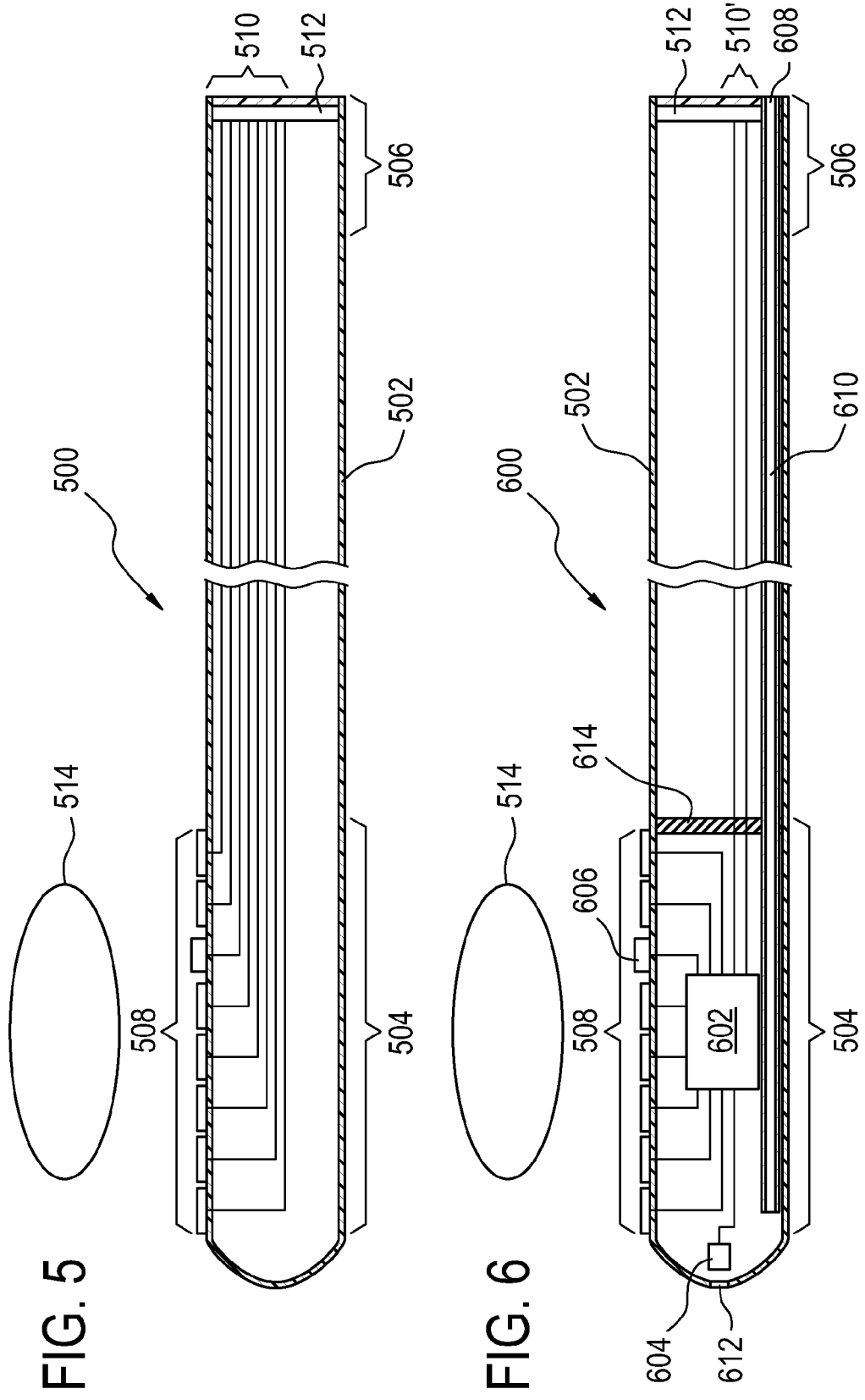

HIGH INTENSITY FOCUSED ULTRASOUND WITH CAPACITIVE MICROMACHINED TRANSDUCERS

CROSS-REFERENCE TO PRIOR APPLICATIONS

This application is the U.S. National Phase application under 35 U.S.C. § 371 of International Application No. PCT/IB2013/052814, filed on Apr. 9, 2013, which claims the benefit of U.S. Provisional Patent Application No. 61/623,123, filed on Apr. 12, 2012. These applications are hereby incorporated by reference herein.

TECHNICAL FIELD

The invention relates to high intensity focused ultrasound, in particular to the use of capacitive micromachined ultrasound transducers for high intensity focused ultrasound.

BACKGROUND OF THE INVENTION

High-intensity focused ultrasound (HIFU) ablation of the prostate has conventionally been done through the rectal wall with a transrectal probe. Alternatively, ablation can also be done through the wall of the urethra using a transurethral probe. The transurethral approach has several safety-related advantages as compared to the transrectal approach. Because the location of the urethra is known (probe within urethra), it is easier to avoid unintentional thermal damage to the urethra that might increase the risk of incontinency. Moreover, since there is no sonication through the rectal wall, the risk of damaging this sensitive structure is also significantly reduced. The main disadvantage of the transurethral approach is that the space available for the transducer is substantially reduced as compared to the transrectal approach. This basically limits the catheter transducer design to one dimensional phased arrays if employing conventional piezoceramic or piezocomposite transducers. This may also limit the possible sonication methods that can be used. For practical reasons, traditional transducers are ridged with a relative low number of large elements, arranged in a row, i.e. a linear (one dimensional) array.

SUMMARY OF THE INVENTION

The invention provides for a medical instrument, a computer program product, and a method of controlling a medical instrument in the independent claims. Embodiments are given in the dependent claims.

A 'capacitive micromachined ultrasonic transducer' (CMUT) as used herein encompasses a capacitive ultrasound transducer that has been manufactured using micromachining technologies. Micromachining technologies are thin film manufacturing techniques; typically they are performed using processes identical to or similar to those used for manufacturing integrated circuits.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging (MRI) image is defined herein as being the reconstructed two or three dimensional visualization of anatomic data contained within the magnetic resonance imaging data. This visualization can be performed using a computer.

Thermal magnetic resonance data is defined herein as being the recorded measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonant frequency. A thermal map, temperature map, or thermographic magnetic resonance image may be reconstructed from the thermal magnetic resonance data.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonant frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM) memory, Read Only Memory (ROM) memory, an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'computer' as used here encompasses and device comprising a processor. A processor is an electronic component which is able to execute a program or machine executable instruction. References to the computing device comprising "a processor" should be interpreted as possibly containing more than one processor. The term computing device should also be interpreted to possibly refer to a collection or network of computing devices each comprising a processor. Many programs have their instructions performed by multiple processors that may be within the same computing device or which may even distributed across multiple computing device.

A 'user interface' as used herein is an interface which allows a user or operator to interact with a computer or computer system. A user interface may provide information or data to the operator and/or receive information or data from the operator. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of receiving information or data from an operator.

In one aspect the invention provides for a medical instrument comprising a high-intensity focused ultrasound system comprising an ultrasound transducer with an adjustable sonication frequency for focusing ultrasound into a sonication volume. The ultrasound transducer comprises a first array of capacitive micromachined transducers. The medical instrument further comprises a processor for controlling the medical instrument. The medical instrument further comprises a memory for storing machine executable instructions. Execution of the instructions causes the processor to receive a treatment plan descriptive of a target zone within a subject. The treatment plan may in some embodiments contain instructions which the processor may use to control the high-intensity focused ultrasound system to sonicate the target zone. In some other embodiments the treatment plan contains data which may be used to generate such commands for controlling the high-intensity focused ultrasound system to sonicate the target zone.

Execution of the instructions further cause the processor to determine a traversal distance through the subject to the target zone using the treatment plan. The traversal distance is descriptive of the traversal ultrasound from the ultrasonic transducer to the target zone. In different embodiments the traversal distance may take different forms or incorporate other data. For instance in some cases a catheter which comprises the ultrasonic transducer may be placed within a subject. In this case the traversal distance would be from a surface interior or exterior of the subject to the target zone. In other embodiments there may be such things as a gel pad and/or water tank in between the transducer and the subject. Execution of the instructions further causes the processor to determine a sonication frequency using the traversal distance for focusing the sonication volume onto the target zone. In some instances focusing the sonication volume onto the target zone may include choosing the frequency so that a larger portion of the ultrasonic energy is deposited in the target zone than in surrounding tissue. Execution of the instructions further cause the processor to sonicate the target zone using the high-intensity focused ultrasound system at the sonication frequency. In some embodiments all of the capacitive micromachined transducers may be operated at the same sonication frequency. In other embodiments only a portion of the capacitive micromachined transducers may be operated at a given sonication frequency, whereas other elements are operated at another frequency or frequencies.

This embodiment may be beneficial because the capacitive micromachined transducers have an extremely large bandwidth which enables a range of frequencies. The frequency of the ultrasound affects at what depth its energy is deposited in the subject. Therefore, choosing the frequency within the bandwidth the amount of energy deposited in the target zone may be maximized.

This embodiment may also be beneficial because the temperature gradient between the target zone and protected zone can be maximized. The protected zone is a region of the subject which is not desirable to heat or for which the temperature remains below a predetermined safety threshold.

In another embodiment the medical instrument further comprises a magnetic resonance imaging system for acquiring magnetic resonance data from an imaging zone. The target zone is within the imaging zone. Execution of the instructions further cause the processor to repeatedly acquire the magnetic resonance data using the magnetic resonance imaging system to reconstruct a magnetic resonance image. The method further comprises the step of modifying the treatment plan in accordance with the magnetic resonance image. This embodiment may be beneficial because the magnetic resonance imaging system enables adjustment and control of the treatment plan. The magnetic resonance imaging system may be part of a closed control loop.

In another embodiment the magnetic resonance data comprises thermal magnetic resonance data. The magnetic resonance image is a thermographic magnetic resonance image.

This embodiment may be beneficial because the magnetic resonance system is measuring the thermographic magnetic resonance image which may be used to drive temperature maps. The temperature maps may be used to directly check the effectiveness of the sonication.

In another embodiment execution of the instructions further cause the processor to acquire planning magnetic resonance data using the magnetic resonance imaging system. Execution of the instructions further causes the processor to reconstruct a planning magnetic resonance image. Execution of the instructions further cause the processor to modify the treatment plan in according with the planning magnetic resonance image. The planning magnetic resonance data is magnetic resonance data that is acquired prior to performing the sonication. It may for instance be used to modify or register the treatment plan. The planning magnetic resonance image is a magnetic resonance image which is used for initial planning or registration with the treatment plan. The subject may be in a different position from when the treatment plan was devised or created. Registering or modifying the treatment plan using the planning magnetic resonance image may help with alleviating errors due to the internal geometry of the subject being poorly aligned with the ultrasound transducer or with the tissue parameters being different than expected or modified as a result of the heating.

In another embodiment the medical instrument further comprises a second array of capacitive micromachined transducers. In some embodiments the first and second arrays of the capacitive micromachined transducers may be operated at the same or different frequencies. This may be beneficial because the ultrasound from each of the transducers may be used to direct ultrasound independently. If there are different frequencies, as long as they are not harmonics, the ultrasound from each of the two capacitive micromachined transducer arrays may be superimposed on the subject independently.

In another embodiment each of the capacitive micromachined ultrasound transducers has a separately controllable sonication frequency. Execution of the instructions causes the processor to determine the sonication frequency for each of the capacitive micromachined ultrasound transducer elements. The capacitive micromachined ultrasound transducers in this embodiment may be individual capacitive micromachined ultrasound transducers from the first and/or second array of capacitive micromachined ultrasound transducers.

In another embodiment execution of the instructions causes the processor to determine a first sonication frequency using the traversal distance for focusing the sonication volume into the target zone. The first sonication frequency may be used as a sonication frequency of the first array of capacitive micromachined transducers. In this case the traversal distance may in fact be a first traversal distance and may represent the distance or be descriptive of the distance between the first array of capacitive micromachined transducers and the target zone. Execution of the instructions further causes the processor to determine a second sonication frequency using the traversal distance for focusing the sonication volume into the target zone. In this case the second sonication frequency may be a sonication frequency used for the second array of capacitive micromachined transducers and the traversal distance may be representative of or descriptive of the distance between the second array of capacitive micromachined transducers and the target zone.

Execution of the instructions causes the processor to sonicate the target zone using the high-intensity focused ultrasound system using the first sonication frequency for the capacitive micromachined transducer array and using the second sonication frequency for the second capacitive micromachined transducer array. The sonication frequency of the previously mentioned embodiments may in fact be either the first sonication frequency or the second sonication frequency referred to in this embodiment. This embodiment may be beneficial because when the two arrays of capacitive micromachined transducers are operated on different frequencies the ultrasound generated by each one may not add constructively or destructively to each other. It may depends upon whether one is a harmonic of the other one. It may also depend upon the distance of the point studied to the transducer elements. If not a harmonic, constructive or destructive resonance may occur at a given point in time, but will also be for a small moment only. The different frequencies may produce a temporal beating pattern in the ultrasound intensity.

In another embodiment the sonication frequency is determined using an ultrasound simulation model. For instance a computer code which performs a finite difference for modeling the simulation or a ray tracing or some other simulation method may be used to determine the frequency. For instance the model could be used to choose a sonication frequency that maximizes or increases the heating in one region. In other embodiments the model may be used to maximize or increase the difference in heating between one region and another region of the subject. This may be particularly beneficial when there is a region of the subject which it is desired not to heat or keep below a certain temperature.

In another embodiment the medical instrument further comprises a catheter. The catheter comprises the ultrasound transducer. This embodiment may be beneficial because the capacitive micromachined ultrasound transducers are small enough that they may be placed on a catheter. This may enable a catheter which may have electronic steering of the sonications which also has an adjustable sonication frequency.

In another embodiment the catheter further comprises a shaft with a distal end and a proximal end. The distal end comprises the first capacitive micromachined ultrasound transducer array and the second capacitive micromachined ultrasound transducer array. The catheter further comprises a connector at the proximal end for supplying the first capacitive micromachined ultrasound transducer array and the second capacitive micromachined ultrasound transducer array with electrical power and for controlling the first sonication frequency and the second sonication frequency. This embodiment may be beneficial because it provides for a catheter which has different arrays of capacitive micromachined ultrasound transducers which can be independently controlled. This may result in more accurate or effective sonication.

In another embodiment the first capacitive micromachined ultrasound transducer array has a first adjustable focus and the second capacitive micromachined ultrasound transducer array has a second adjustable focus. An adjustable focus as used herein encompasses electronic control of the focus. There are multiple individual arrays. The phase and/or amplitude may be controlled individually for each of the individual capacitive micromachined transducers. The constructive and destructive interference of the ultrasound generated by each of the capacitive micromachined transducers allows the sonication volume to be slightly shifted or moved. In combination with changing or adjusting the frequency this enables much more detailed control of the sonication volume. In the case where the first sonication frequency and the second sonication frequency are not harmonics or identical the ultrasound from the first array and second array of capacitive micromachined transducers may be directed towards different volumes. In this case the sonication volume would be a superposition of the sonication volume from the first and second arrays of capacitive micromachined transducers.

In another embodiment the distal end comprises at least one integrated circuit for powering the capacitive micromachined ultrasound transducer array and the second capacitive micromachined ultrasound transducer array and for providing electronic control of the capacitive micromachined ultrasound transducer array and the second capacitive micromachined ultrasound transducer array. The catheter further comprises a data bus between the at least one integrated circuit and the connector. The data bus enables a computer or other system to control the integrated circuits. In some embodiments the integrated circuit also provides for allowing the frequency of each of the capacitive micromachined ultrasound transducers to be individually controlled. The individual capacitive micromachined ultrasound transducer may therefore be operated at varying frequencies. This may enable a much greater control of the sonication with the ultrasound transducer.

In another aspect the invention provides for a computer program product comprising machine-executable instructions for execution by a processor controlling the medical instrument. The medical instrument comprises a high-intensity focused ultrasound system comprising an ultrasound transducer with an adjustable sonication frequency for focusing ultrasound into a sonication volume. The ultrasound transducer comprises a first array of capacitive micromachined transducers. Execution of the instructions causes the processor to receive a treatment plan descriptive of a target zone within a subject. Execution of the instructions further cause the processor to determine a traversal distance through the subject to the target zone using the treatment plan. The traversal distance is descriptive of the traversal of ultrasound from the ultrasound transducer to the target zone. Execution of the instructions further causes the processor to determine a sonication frequency using the traversal distance for focusing the sonication volume onto the target zone. Execution of the instructions further causes the processor to sonicate the target zone using the high-intensity focused ultrasound system using the sonication frequency. The benefits of this computer program product have been previously discussed.

In another aspect the invention provides for a method of controlling a medical instrument comprising a high-intensity focused ultrasound system. The high-intensity focused ultrasound system comprises an ultrasound transducer with an adjustable sonication frequency for focusing ultrasound into a sonication volume. The ultrasound transducer comprises a first array of capacitive micromachined transducers. The method comprises the step of receiving a treatment plan descriptive of a target zone within a subject. The method further comprises the step of determining a traversal distance through the subject to the target zone using the treatment plan. The traversal distance is descriptive of the traversal of ultrasound from the ultrasound transducer to the target zone. The method further comprises the step of determining a sonication frequency using the traversal distance for focusing the sonication volume onto the target zone. The method further comprises the step of sonicating the target zone using the high-intensity focused ultrasound system using the sonication frequency. The benefits of this method have been previously discussed.

BRIEF DESCRIPTION OF THE DRAWINGS

In the following preferred embodiments of the invention will be described, by way of example only, and with reference to the drawings in which:

FIG. 5 illustrates a catheter according to a further embodiment of the invention;

FIG. 6 illustrates a catheter according to a further embodiment of the invention;

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
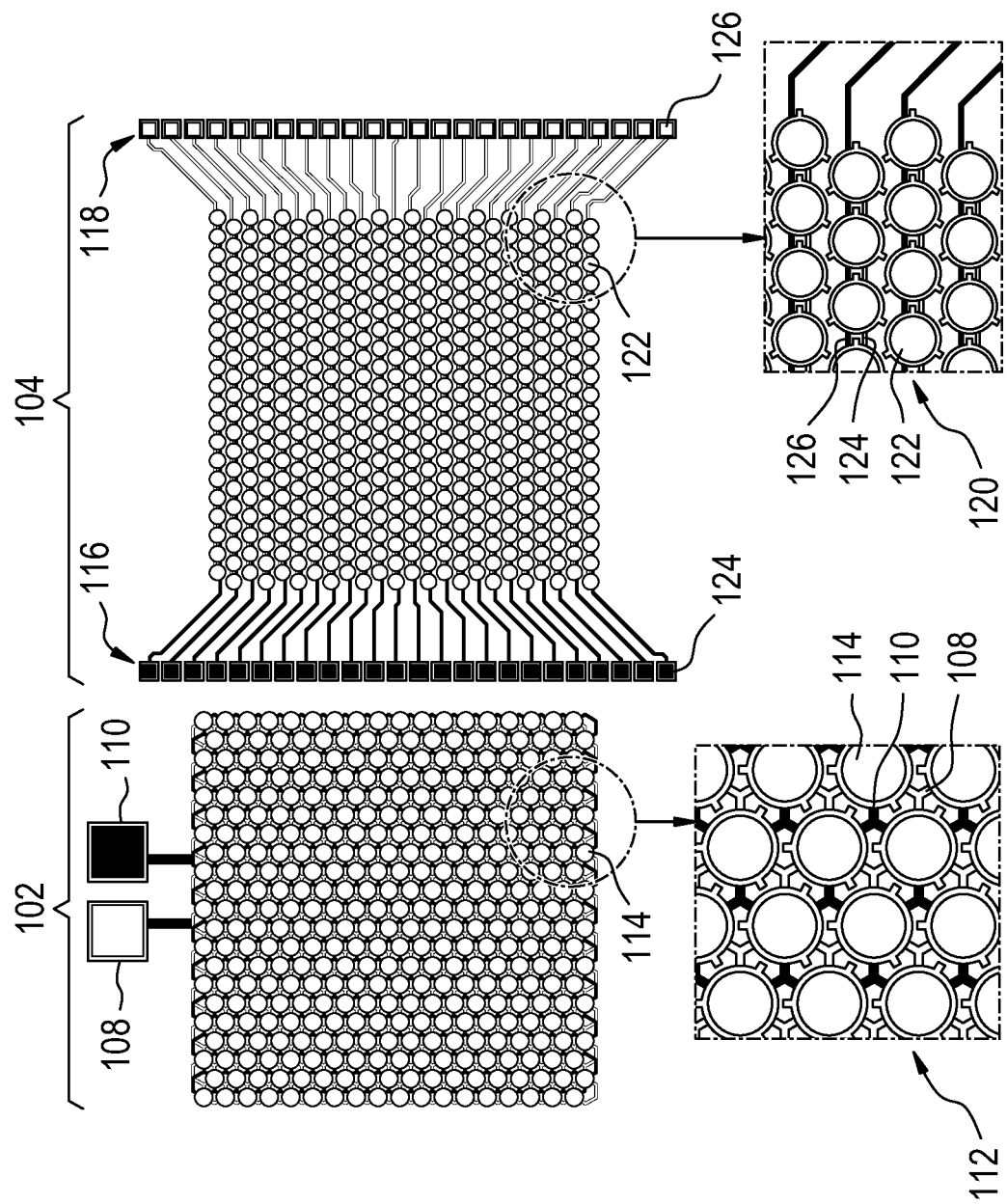
FIG. 1 illustrates two examples of capacitive micromachined ultrasound transducer arrays.

In FIG. 1 two examples of arrays 402, 404 of capacitive micromachined ultrasound transducers are shown. The capacitive micromachined ultrasound transducer array 102 has first 108 and second 110 electrical connections. Array 102 is wired so that it functions as a single transducer element in the way that a traditional piezoelectric element does. Drawing 112 shows a blowup of array 102. The individual capacitive micromachined ultrasound transducers 114 can be seen. It can be seen that each of the transducers 114 is connected to the first 108 and second 110 electrical connections. In this example the resulting array 102 would have a wide bandwidth for the sonication frequency, however individual electronic, phase and amplitude, control of the individual capacitive micromachined ultrasound transducers would not be possible. The bandwidth is mainly determined by the size of the individual elements 114, as well as the thickness of the element membrane.

The array 104 of capacitive micromachined ultrasound transducers is arranged as linear arrays. There is a set of first 116 and second 118 electrical connections for each row of transducers. Drawing 120 is a blowup detail of the array 104. An individual capacitive micromachined ultrasound transducer 122 can be shown as being connected to a first 124 and second 126 electrical connection. The connections 124 and 126 are chosen from the first 116 and second 118 sets of electrical connections. Capacitive micromachined ultrasound transducers making up a linear array would be controlled as a group. The sonication frequency, amplitude, and phase would be determined for an entire array. Other embodiments may also be constructed. For example it is possible to construct an array where the sonication frequency, amplitude, and/or phase are controllable for each individual micromachined ultrasound transducer.

Figure 2:
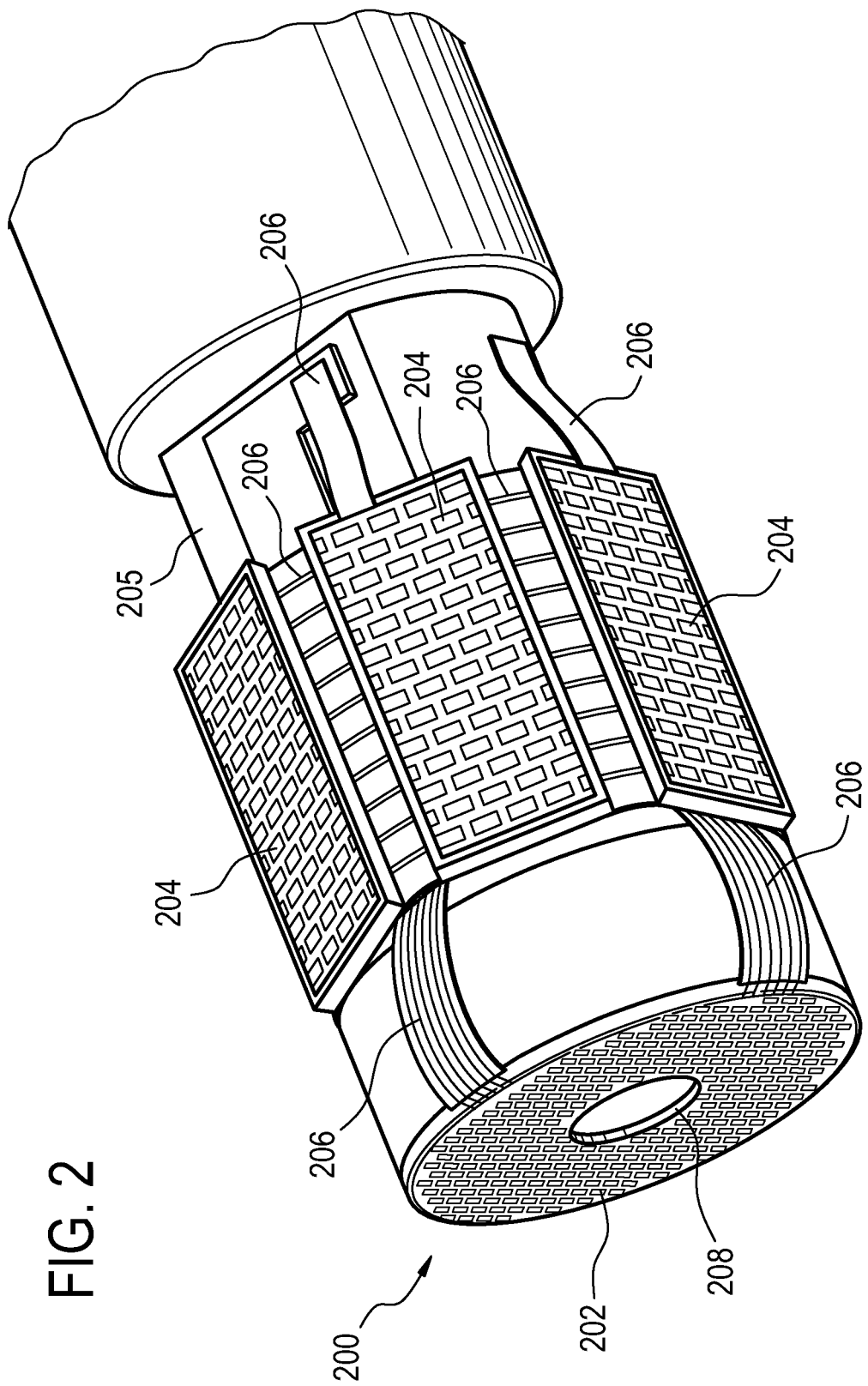
FIG. 2 illustrates a catheter according to an embodiment of the invention.

FIG. 2 shows a distal end 200 of a catheter according to an embodiment of the invention. In this embodiment there is a forward-looking ring array 202. There is an array of capacitive micromachined ultrasound transducers surrounding a hole 208. Behind the ring array 202 are panels of sideways-looking arrays 204. The arrays 204 form a ring around the shaft of the catheter. Shown in this FIG. are various electrical connections 206. The forward-looking ring array 202 may be used for such things as providing three dimensional imaging. The sideways-looking arrays 204 may be used for ultrasound ablation and monitoring. The individual capacitive micromachined ultrasound transducers can be used for beam steering during ultrasound ablation. The frequency of ultrasound supplied to each of the arrays 204 may be independently controlled. Benefits of this embodiment may include that there is no or minimal need for mechanically rotating of the catheter. The hole 208 can be used for additional instruments or for water irrigation. The embodiment shown in FIG. 2 can focus in multiple directions so for such things as ablating a prostate the entire 360 degrees around the probe may be performed simultaneously or with minimal rotation. This would result in less treatment time and thus also reduce costs.

In addition to wiring the capacitive micromachined ultrasound transducers in large block arrays or in linear arrays the individual micromachined ultrasound transducers may also be individually driven by their own source.

Figure 3:
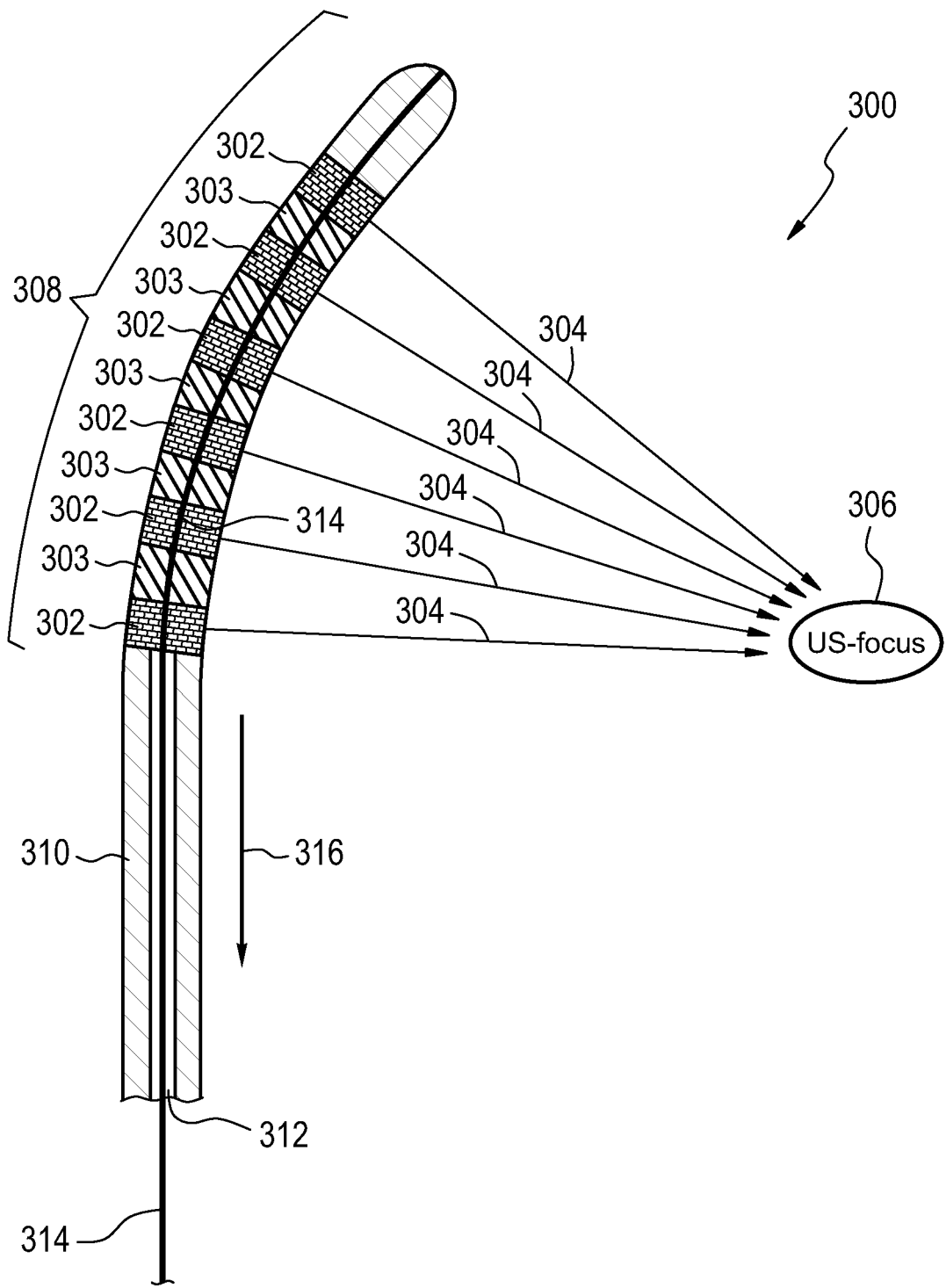
FIG. 3 illustrates a catheter according to a further embodiment of the invention.

FIG. 3 shows a catheter 300 where the focus is adjusted mechanically. The catheter has arrays 302 of capacitive micromachined ultrasound transducers. The arrays in this embodiment may be flexible or they may be rigid. Shown is a flexible element 303 between each of the arrays 302. The lines 304 trace the general path of the ultrasound generated by the arrays 302. The ultrasound 304 concentrates in a target zone 306. All of the arrays 302 are located on the distal end 308 of the shaft 310 of the catheter 300. There is a curvature at the distal end 308. This causes the collection of arrays 302 to focus their ultrasound in the target zone 306. Such an arrangement could be adjusted mechanically. For instance located within the catheter could be a tube 312 which is mounted rigidly or semi-rigidly to the shaft 310. Within the tube 312 could be a cable 314. The cable could extend up from the tube 312 through the distal end 308 of the catheter 300. The distal end 308 could for instance have a springy material or be pre-stressed. This may cause a natural curvature of the distal end 308. When the cable is pulled or moved in the direction 318 this causes the cable 314 to shorten which may cause the distal end 308 to straighten. This would change the focus of the catheter 300. The cable 314 could also be used to manipulate a linkage. The mechanical adjustment of this catheter may be used, in some embodiments, to actively steer or guide the catheter. In other words the mechanical adjustment for the focus may be used to mechanically adjust the position of the distal end. In addition to the mechanical focusing the individual arrays 302 may also have electronic phase and amplitude control in addition to controlling the sonication frequency of each of the arrays 302.

Using FIG. 3 as an example, the lines labeled 304 may also represent a traversal distance 304 between the capacitive micromachined transducers 302. In this case the distal end 308 of the probe is curved such that each of the capacitive micromachined transducers 302 is roughly the same distance from the ultrasound focus 306. In other embodiments the traversal distance 304 may be different for each of the capacitive micromachined transducers 302. During operation a treatment plan descriptive of a target zone or in this case a focus 306 would be received. Next a traversal distance 304 would be determined through the subject to the target zone 306 using the treatment plan. The traversal distance is descriptive of the traversal of ultrasound from the ultrasound transducer to the target zone. In the case of multiple capacitive micromachined transducer arrays the traversal distance may in fact be multiple distances. Next, a sonication frequency for focusing the sonication volume onto the target zone is determined using the traversal distance. In the case of multiple capacitive micromachined transducer arrays there may be an independent frequency calculated for each of the capacitive micromachined transducer arrays. Finally the capacitive micromachined transducer array or arrays are operated at the determined sonication frequency.

Figure 4:
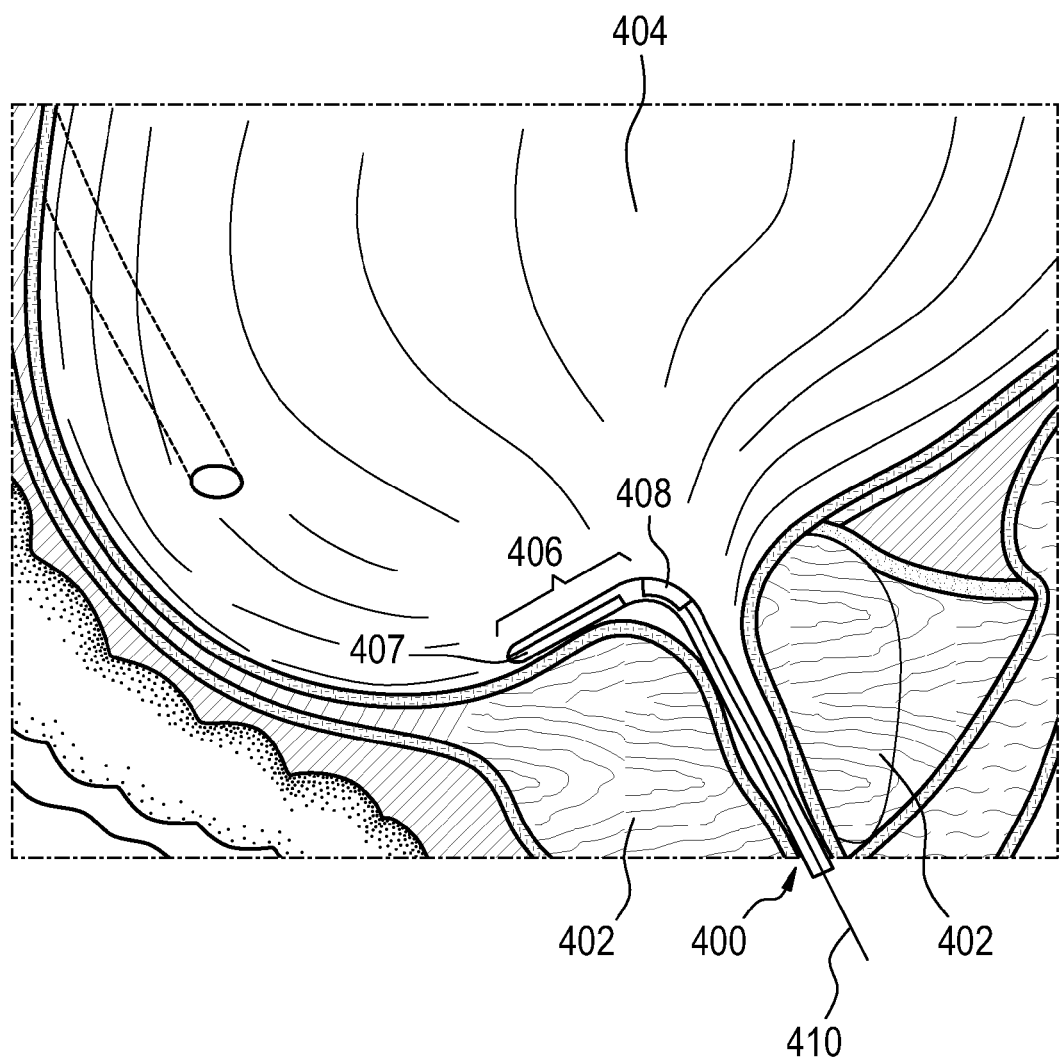
FIG. 4 illustrates the use of a catheter according to a further embodiment of the invention.

FIG. 4 shows a catheter 400 according to an embodiment of the invention being used to treat a prostate 402. The catheter 400 has been inserted through the urethra and into the bladder 404. In this embodiment the distal end 406 of the catheter 400 has an array 407 of capacitive micromachined ultrasound transducers. There is a mechanical actuator 408 which flexes the distal end 406. There is a cable 410 for controlling the mechanical actuator 408. The embodiment shown in FIG. 4 can be shown as being advantageous because the catheter 400 may be inserted into the bladder and then the mechanical actuator 408 is used to position the array of capacitive micromachined ultrasound transducers 407 such that the prostate 402 can be sonicated. A benefit of this embodiment is that the catheter 400 may enable sonication of the prostate from the bladder. The added mechanical freedom in the bladder may aid in positioning the catheter effectively to reach some areas of the prostate and thereby reduce the risk of damaging healthy tissue.

FIG. 5 shows a further embodiment of a catheter 500 according to an embodiment of the invention. The catheter 500 has a shaft 502 with a distal end 504 and a proximal end 506. At the distal end 504 there are multiple arrays 508 of capacitive micromachined ultrasound transducers. Each of the arrays 508 has its own electrical connection 510 to a connector 512 at the proximal end 506. When supplied with electrical power the arrays 508 deposit ultrasonic energy in a target zone 514 which is adjacent to or to the side of the shaft 502.

FIG. 6 shows a further embodiment of a catheter 600 according to an embodiment of the invention. The embodiment shown in FIG. 6 is very similar to that shown in FIG. 5 but several features have been added. In this embodiment the individual arrays 508 are connected to an integrated circuit 602 instead of being connected directly to the connector 512. The integrated circuit 602 is connected to the connector 512 by data bus 510' which functions as supplying both power and a data connection. Via the data bus 510' the integrated circuit 602 receives instructions for how to drive the individual arrays 508. The integrated circuit 602 is also shown as being connected to a pressure or flow sensor 604 at the tip of the proximal end 504. The integrated circuit 602 is also shown as being connected to a temperature sensor 606 which is mounted amongst the arrays 508. Depending upon the embodiment the arrays 508 and the integrated circuit 602 can be used for ablation and/or for performing diagnostic ultrasound. In some embodiments some of the arrays 508 may be used for performing ablation and some may be used for performing diagnostic ultrasound at the same time. At the connector 512 is also a fluid cooling inlet 608. The fluid cooling inlet 608 is connected to a tube 610 which is adapted for carrying cooling fluid to the proximal end 504 for cooling it. At the tip of the proximal end 504 is an outlet 612. The proximal end 504 is closed off with a seal 614 so that cooling water or cooling fluid which comes in the tube 608 is forced out through the outlet 612. In other embodiments there may be a return tube and a fluid cooling outlet at the connector 512.

Figure 7:
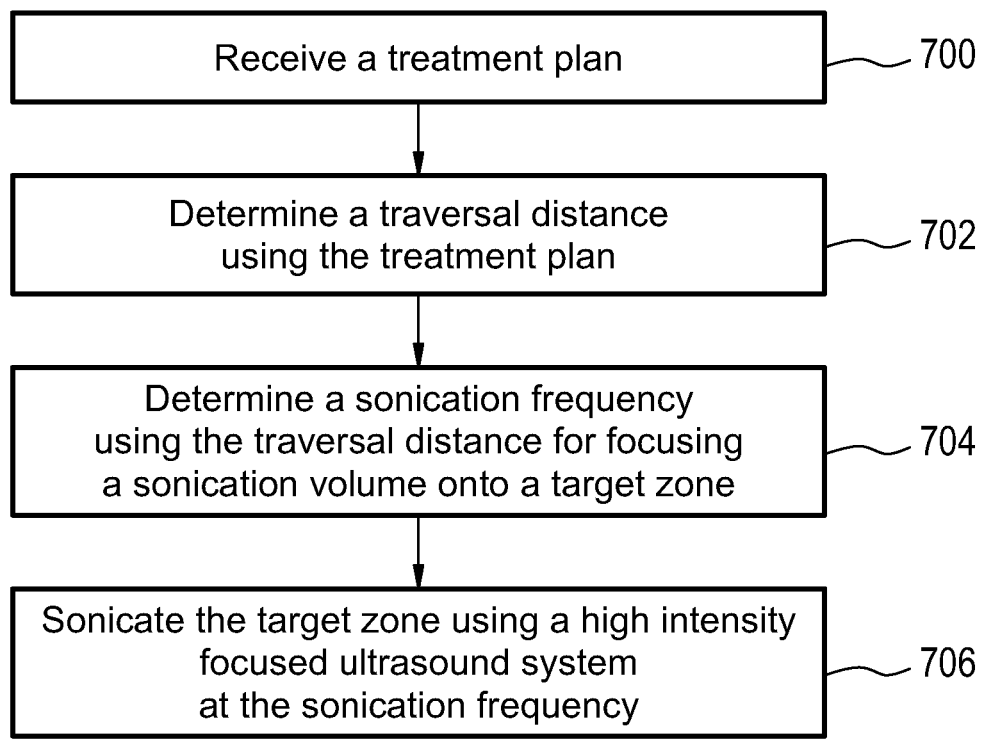
FIG. 7 illustrates flow chart according to an embodiment of the invention.

FIG. 7 shows a flow diagram which illustrates a method according to an embodiment of the invention. First in step 700 a treatment plan is received. The treatment plan is descriptive of a target zone within a subject. Next in step 702 a traversal distance is determined using the treatment plan. The traversal distance is descriptive of the traversal of ultrasound from the ultrasound transducer to the target zone.

Next in step 704 a sonication frequency is determined using the traversal distance for focusing a sonication volume onto a target zone. Finally in step 706 the target zone is sonicated using a high-intensity focused ultrasound system at the sonication frequency.

Figure 8:
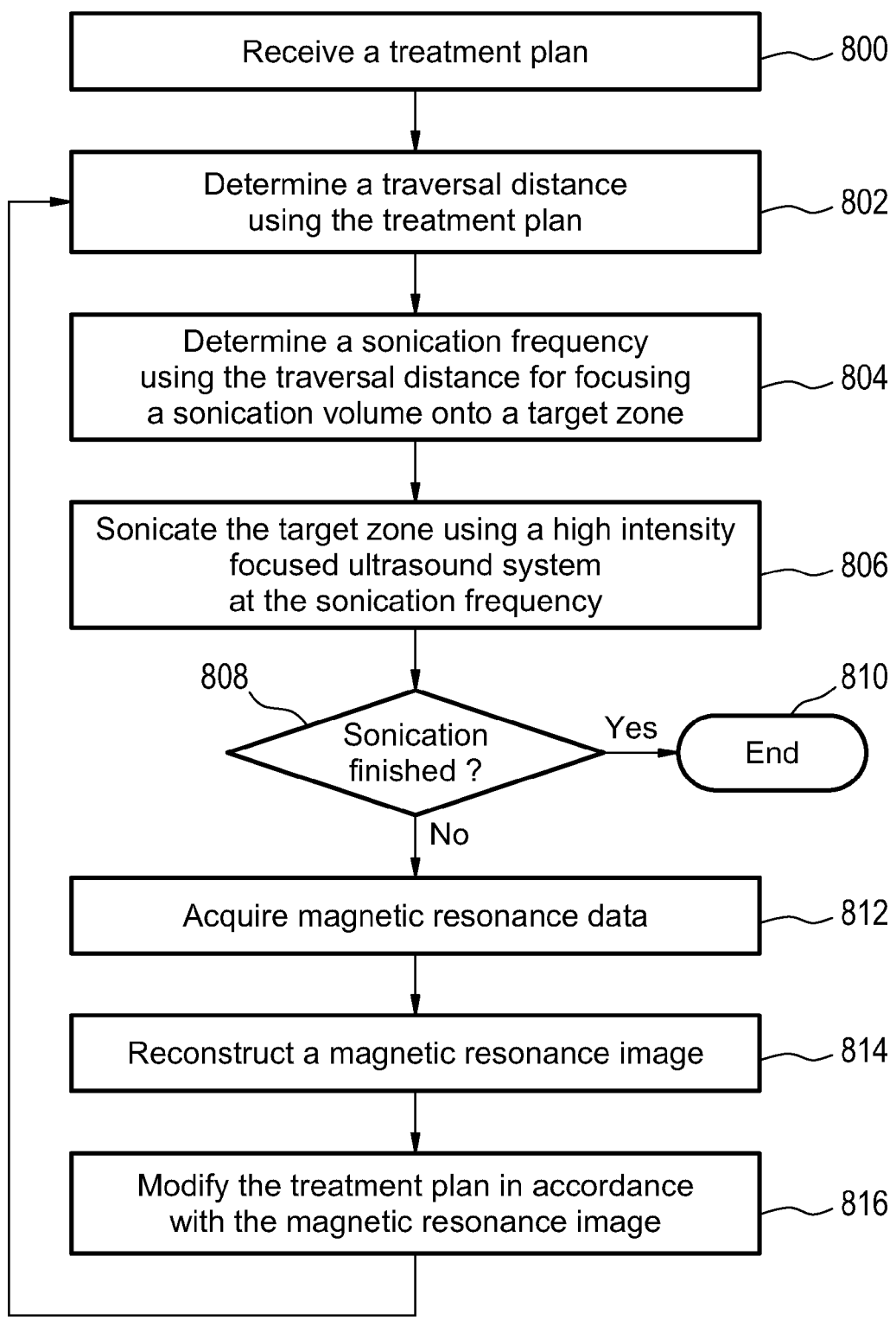
FIG. 8 illustrates flow chart according to a further embodiment of the invention.

FIG. 8 shows a flow diagram which illustrates a method according to a further embodiment of the invention. First in step 800 a treatment plan is received. Again the treatment plan is descriptive of a target zone within a subject. Next in step 802 a traversal distance is determined using the treatment plan. The traversal distance is descriptive of the traversal of ultrasound from the ultrasound transducer to the target zone. Next in step 804 a sonication frequency is determined using the traversal distance for focusing a sonication volume on a target zone. Next in step 806 the target zone is sonicated using a high-intensity focused ultrasound system at the sonication frequency. Step 808 is a decision box and the question is is the sonication finished. If the sonication is finished then the method proceeds to step 810 which is the end. The sonication at this point ceases. If the sonication is not finished the method proceeds to step 812. In step 812 magnetic resonance data is acquired. This may be acquired using a magnetic resonance imaging system. Next in step 814 a magnetic resonance image is reconstructed using the magnetic resonance data. In some embodiments the magnetic resonance data may comprise magnetic resonance data. In this case the magnetic resonance image may comprise a thermal map. Next in step 816 the treatment plan is modified in accordance with the magnetic resonance image. For instance if the subject has moved during the therapy or if certain regions of the subject are too hot or have not been heated enough the treatment plan may be adjusted or changed. The method then returns to step 802 and a traversal distance is again determined using the treatment plan. The method thus continues in a loop until in step 808 it is determined if the sonication is finished and the method ends at step 810.

Figure 9:
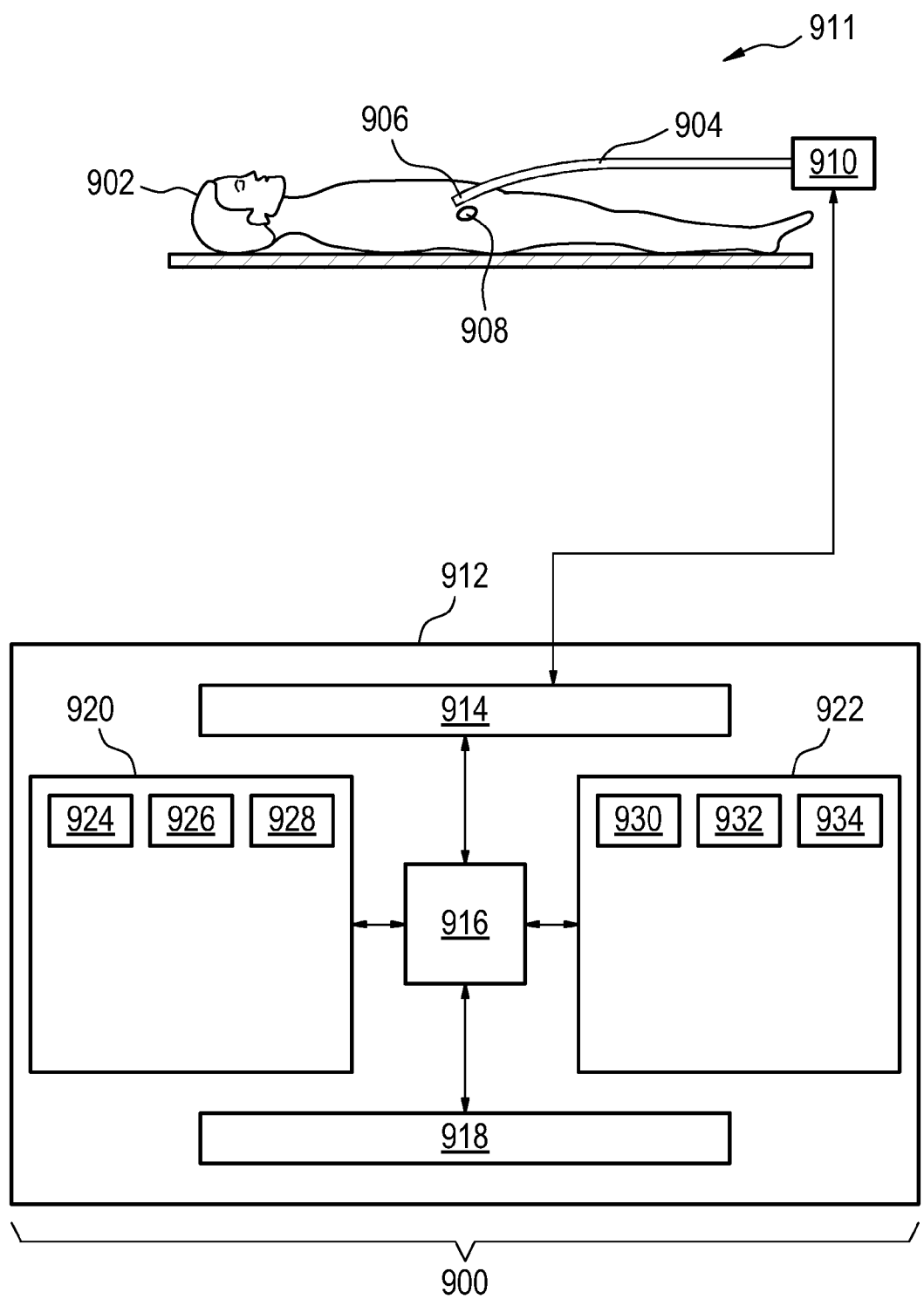
FIG. 9 illustrates a medical instrument according to an embodiment of the invention.

FIG. 9 illustrates a medical instrument 900 according to an embodiment of the invention. Shown in this FIG. is a subject 902 with a catheter 904 inserted. The catheter 904 has a distal distance 906 in the proximity of a target zone 908. The catheter 904 may be of a type illustrated in the previous embodiments. The catheter 906 is connected to a catheter interface 910. The catheter interface 910 provides a control and power supply function for the catheter 904. The high-intensity focused ultrasound system 911 is a combination of the catheter 904 and the catheter interface 910. Other types of high-intensity focused ultrasound systems may also be implemented. For instance an array used for treating a breast where a breast is inserted into a cup-like structure surrounded by arrays of capacitive micromachined transducers is also an embodiment according to the invention. Likewise a large ultrasound transducer may also be fashioned out of capacitive micromachined transducers and using in a system which is similar to those used for heating uterine fibroids.

In this embodiment the catheter interface 910 is connected to a hardware interface 914 of a computer 912. The computer 912 further comprises a processor 916 which is in communication with the hardware interface and also a user interface 918, computer storage 920 and computer memory 922. The processor 916 is able to control the operation and function of the catheter interface 910 via the hardware interface 914.

The computer storage is shown as containing a treatment plan 924. The computer storage is further shown as containing a traversal distance 926 that was calculated using the treatment plan 924. The computer storage 920 is further shown as containing a sonication frequency 928 which is calculated using the traversal distance 926.

The computer memory 922 is shown as containing a traversal distance calculation module 930. The traversal distance calculation module 930 contains computer-executable code which enables the processor to calculate the traversal distance 926 using the treatment plan 924. The computer memory 922 is shown as further containing a sonication frequency determination module 932. The sonication frequency determination module 932 further contains machine-executable instructions which enable the calculation of the sonication frequency 924 using the traversal distance 926. The computer memory 922 is shown as further containing high-intensity focused ultrasound system control module 936. The high-intensity focused ultrasound system control module 934 contains computer-executable code which enables the processor 916 to generate commands which enable using the treatment plan 924 which enable to control the catheter interface 910.

In using such a medical instrument 900 an operator may insert the catheter 904 into the subject 902. As the focus of the catheter 904 is adjustable the processor 916 is able to send commands to the catheter interface 910 such that the target zone 908 is heated by the catheter 904. The target zone is controllably heated by the catheter 904 and is automatically controlled by the computer system 912.

Figure 10:
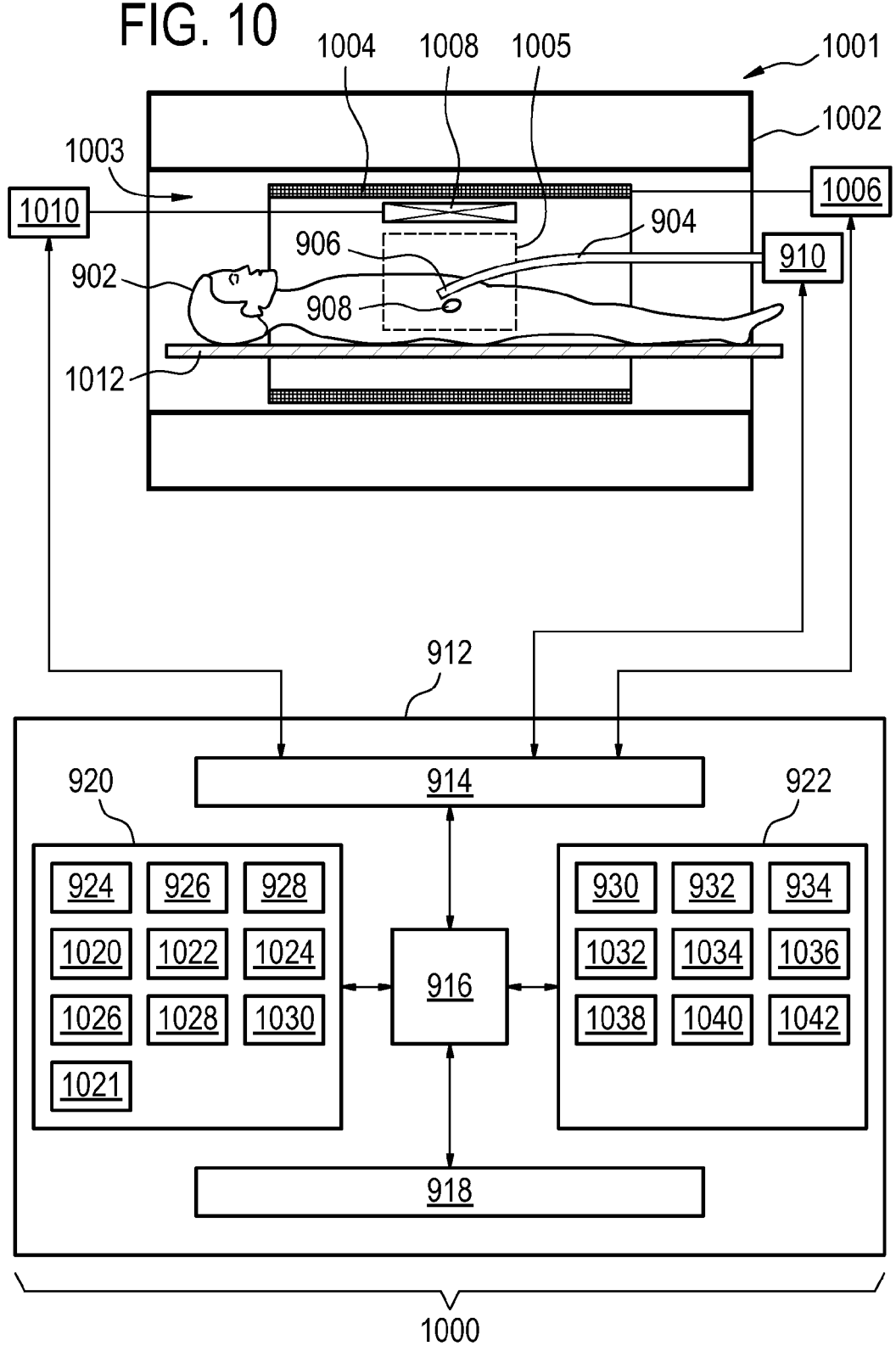
FIG. 10 illustrates a medical instrument according to a further embodiment of the invention.

FIG. 10 shows a medical instrument 1000 according to a further embodiment of the invention. The medical instrument 1000 shown in FIG. 10 is similar to that shown in FIG. 9 except there is additionally a magnetic resonance imaging system 1001

The magnetic resonance imaging system 1001 comprises a magnet 1002. The magnet 1002 is a cylindrical type superconducting magnet. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone 1005 where the magnetic field is strong and uniform enough to perform magnetic resonance imaging.

Within the bore of the magnet 1003 there is a magnetic field gradient coil 1004 which is supplied current by a magnetic field gradient coil power supply 1006. The magnetic field gradient coil 1004 is used to spatially encode magnetic spins within the imaging zone 1005 of the magnet 1002 during the acquisition of magnetic resonance data. The magnetic field gradient coil 1004 is intended to be representative. Typically magnetic field gradient coils contain three separate sets of coils for spatially encoding in three orthogonal spatial directions. The current supplied to the magnetic field coil 1004 is controlled as a function of time and may be ramped or pulsed.

Within the bore of the magnet 1003 is an imaging zone 1005 where the magnetic field is uniform enough for performing magnetic resonance imaging. Adjacent to the imaging zone 1005 is an antenna 1008. The antenna 1008 is connected to transceiver 1010. The radio frequency antenna 1008 is for manipulating the orientations of magnetic spins within the imaging zone 1005 and for receiving radio transmissions from spins also within the imaging zone. The radio frequency antenna may contain multiple coil elements. The radio frequency antenna may also be referred to as a channel. The radio frequency coil is connected to a radio frequency transceiver 1010. The radio frequency coil 1008 and radio frequency transceiver 1010 may be replaced by separate transmit and receive coils and a separate transmitter and receiver. The radio frequency antenna is intended to also represent a dedicated transmit antenna and a dedicated receive antenna. Likewise the transceiver 1010 may also represent a separate transmitter and receivers.

The subject 902 is seen as reposing on subject support 1012. As in FIG. 9 the catheter 904 has been inserted into the subject 902. The transceiver 1010, the gradient coil power supply 1006 and the catheter interface 904 are all shown as being connected to the hardware interface 914 of computer system 912. The computer system 912 in FIG. 10 is equivalent to the computer system 912 in FIG. 9. The various software components stored in computer memory 922 and the contents of the computer storage 920 are equivalent in the two Figs.

The computer storage 920 is shown as additionally containing a pulse sequence 1020. The pulse sequence 1020 is a set of commands which the processor 916 can either use to control the magnetic resonance imaging system 1001 or may be used to generate commands for controlling the magnetic resonance imaging system 1001. The computer storage 920 is shown as additionally containing magnetic resonance data 1021 that was acquired using the pulse sequence 1020. The computer storage 920 is also shown as containing thermal magnetic resonance data 1022 that may also have been acquired using the pulse sequence 1020. The computer storage 920 is shown as containing a magnetic resonance image 1024 that was reconstructed using the magnetic resonance data 1021. The computer storage 920 is further shown as containing a thermographic magnetic resonance image 1026 that was reconstructed using the thermal magnetic resonance data 1022. The computer storage 920 is further shown as containing planning magnetic resonance data 1028. The computer storage 920 is further shown as containing planning magnetic resonance image 1030 that was reconstructed using the planning magnetic resonance data 1028.

The computer memory 922 is shown as containing a magnetic resonance imaging system control module 1032. The magnetic resonance imaging system control module 1032 contains computer-executable code which enables the processor 916 to use the pulse sequence 1020 to generate commands for controlling the operation and function of the magnetic resonance imaging system 1001. The computer memory 922 further contains an image reconstruction module 1034. The image reconstruction module 1034 contains computer-executable code which enables the processor 916 to reconstruct the magnetic resonance image 1024 from the magnetic resonance data 1021. The magnetic resonance imaging system control module 1032 may also be used to generate or reconstruct the planning magnetic resonance image 1030 from the planning magnetic resonance data 1028. The computer memory 922 is shown as further containing a thermal mapping module 1036. The thermal mapping module 1036 contains computer-executable code which enables the processor 916 to generate the thermographic magnetic resonance image 1026 from the thermal magnetic resonance data 1022.

The computer memory 922 further contains a treatment plan modification module 1038. The treatment plan modification module 1038 enables the processor 916 to modify the treatment plan 924 using the magnetic resonance image 1024, the thermographic magnetic resonance image 1026, and/or the planning magnetic resonance image 1030. The computer memory 922 is shown as further containing an image registration module 1024. The image registration module 1024 contains computer-executable code that may be used by the processor 916 for registering the magnetic resonance image 1024, the thermographic magnetic resonance image 1026, and/or the planning magnetic resonance image 1030 with the subject 1002. The image registration module 1040 may for instance be used by the treatment plan modification module 1038. The computer memory 922 is also shown as containing an ultrasound simulation module 1042. The ultrasound simulation module 1042 contains computer-executable code which enables the processor 916 to simulate the effects of ultrasound generated by the catheter 906. The ultrasound simulation module 1042 may be used in conjunction with the treatment plan modification module 1038.

Conventionally, piezoceramic or piezocomposite transducers have been used in transurethral HIFU. This more or less means that only a 1D phased-array is possible due to the limited space available within the urethra. With CMUT technology this is no longer the case and 2D arrays may easily fit within the urethra and these are also highly steerable arrays. This enables the use of more sophisticated sonication methods, and also enables the use of more sophisticated feedback methods. Beam steering and trajectories are made possible with some practical limitations, and the frequency can moreover be altered rapidly and through a continuous frequency band with no alterations of the electronics being required. Hence, more complex feedback algorithms can be devised for prostate ablation that have previously not been possible. Moreover, the sonication can be made and controlled in several radial directions simultaneously if the catheter cross-section is for example hexagon shaped.

Capacitative micromachined transducers (CMUTs) has recently shown promise for transurethral prostate HIFU ablation. The frequency band width possible to achieve with CMUTs is typically higher than for piezo transducers, which makes the CMUTs more adapt for applications where a larger range of penetration depths are required. These CMUTs also bring a new range of capabilities that enable new ways of doing transurethral HIFU ablation.

1D phased-arrays, as are typically constructed using piezoelectric arrays, only allow a very coarse feedback control where the power may be varied element by element along the phased-array. 2D phased-array piezo transducers are in turn difficult to fit within the space of the urethra. CMUT 2D-arrays have a smaller element size allowing them to fit within the urethra and can also have several other benefits.

Beam steering may be made possible within the prostate with a transurethral CMUT. This in turn enables control algorithms to be used for transurethral prostate that are conventionally only applied to HIFU therapies using external transducers. For example, the temperature and/or thermal dose may be controlled in the different parts of the prostate by defining areas to avoid and then defining which areas to ablate (commonly the remaining part of the prostate in case of whole gland therapy). Different versions of a 2D or 3D PID controller can for example be used or by heating those areas within the current heated volume that have the largest temperature deficiency compared to the target temperature. The latter approach also requires taking into account the energy possible to deliver before the next temperature update is obtained. The method in itself is rather well known already, and other methods of feedback control may also be used.

CMUTs may also enable choosing the frequency freely within the bandwidth of the transducer which is typically quite large. Piezo-based transducers can have a few (for example most commonly 1 or 2) discrete frequencies to choose from at most. This allows for altering yet another parameter. The equation for local absorbed ultrasound energy when assuming a loss only through absorption (i.e. equating attenuation coefficient with the absorption coefficient) for a planar wave in a single tissue is:

$$Q = 2\alpha f e^{-2\alpha f x} \frac{p^2}{\rho c}$$

where p is the pressure at the surface of the tissue, f is the ultrasound frequency, x is the distance traveled in said tissue, and σ is the density, c the speed of sound, α the absorption (equaled to attenuation) of the tissue in question.

Figure 11:
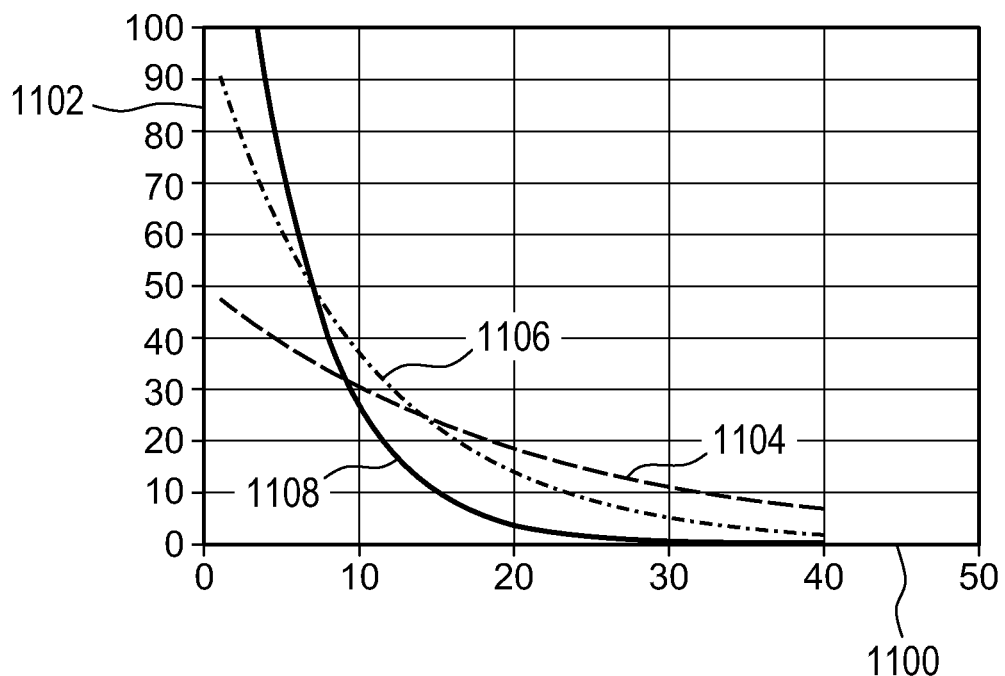
FIG. 11 shows the absorbed ultrasound energy as a function of depth in millimeters.

This relation is plotted in FIG. 11. FIG. 11 shows the absorbed ultrasound energy 1102 as a function of depth 1100 in millimeters. These are calculated values assuming a linear dependency of the absorption on the attenuation. Three values are plotted: absorption at 5 MHz 1104, 10 MHz 1106, and 20 MHz 1108. At shallow depths the highest 20 MHz 1108 frequency has the best absorption, whereas at intermediate depths 10 MHz 1106 is superior and deeper than 15 mm the 5 MHz 1104 frequency is the best. An alpha of 5 Np/MHz/m was assumed in this example.

For a certain depth x, there is an optimal frequency that maximizes the absorbed amount of US energy which is given by:

$$f_{max} = \frac{1}{2\alpha x},$$

and still uses the assumption that the absorption scales linearly with the frequency. Even if this assumption was not to hold entirely, there is an optimal frequency for maximizing the absorption and the longer the penetration depth desired the lower the frequency should be.

Figure 12:
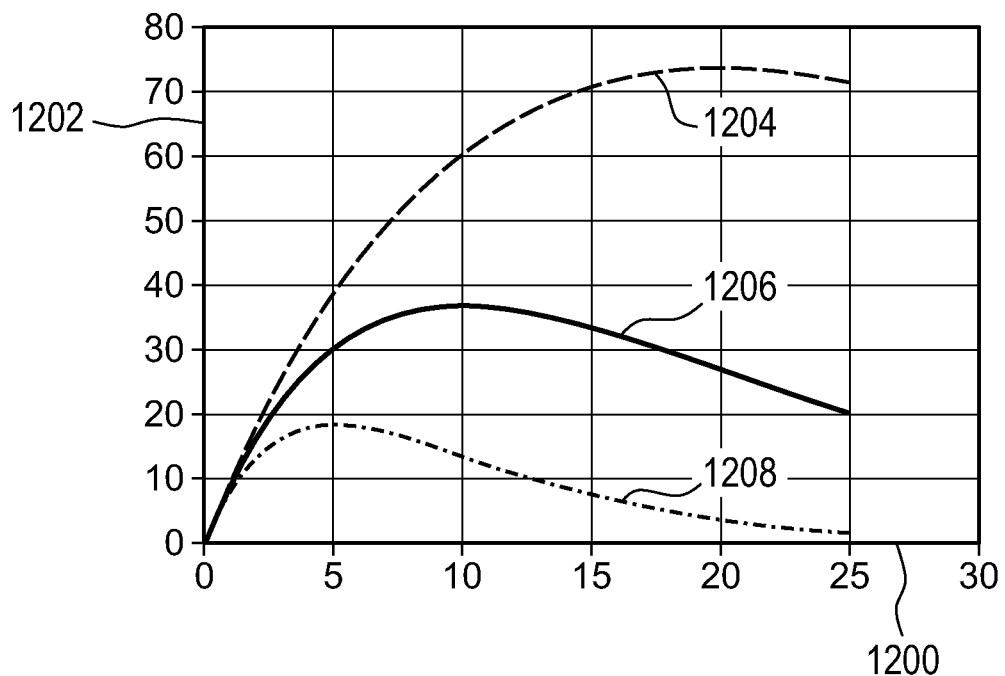
FIG. 12 shows the absorbed ultrasound energy as a function of frequency at three different depths.

FIG. 12 shows the absorption at a given target depth as a function of frequency. FIG. 12 shows the absorbed ultrasound energy 1202 as a function of frequency 1200 at three different depths. The curve labeled 1204 is at 5 mm, the curve labeled 1206 is at 10 mm, and the curve at 20 mm is 1208. At 5 mm 1204 the maximum absorption appears to be at 20 MHz, at 10 mm 1206 the maximum absorption is 10 MHz, and at 5 mm 1204 the maximum absorption is at 20 MHz in this example. An alpha of 5 Np/MHz/m was assumed in the example also.

It is not necessarily so that the frequency giving the highest absorption is preferable if for example close to the prostate capsule. In such a case, it may be that a frequency that gives a quicker drop-off in absorbed energy is preferable to keep the capsule and any potential sensitive tissues directly outside the prostate from heating too much. Again assuming a linear relationship, the maximum drop-off in absorption (maximum of the derivative of the absorption) at a certain distance is obtained at twice the frequency giving the maximum absorption.

Finally, heating in several directions may be done simultaneously if more than one radial direction is covered by CMUT elements. The segment of the prostate heated by each heating 2D array, for example 8 in case of a hexagonal cross-section, can be controlled individually as described above in 2D or 3D depending on the MR images acquired.

Embodiment of the invention may comprise a control algorithm which may allow the frequency to be one of the control variables. Conventional piezo transducers may only have a few discrete frequencies that can be used, while CMUTs have a broad continuous frequency band from which to choose. Switching frequency may typically require a few ultrasound (US) cycles to get to full output pressure at the new frequency. This duration is similar to if the phase of the elements is changed during electronic steering. FIGS. 11 and 12 shows that substantial improvements can be obtained in the absorption by altering the frequency used. It is not necessarily so that the frequency giving the highest absorption is preferable if for example close to the prostate capsule. In such a case, it may be that a frequency that gives a quicker drop-off in absorbed energy is preferable to keep the capsule from heating too much. Similar may apply close to the nerve bundles. The best frequency might be somewhere between the two frequencies as the frequency providing the maximum drop-off speed will be higher than the frequency giving the maximum absorption. Acoustic and thermal simulations may also aid in providing an estimate of the best frequency to be used.

The altering of the sonication frequency may be of particular value for short penetration depths and also in case steering is limited by a small dimension of the 2D array in one direction. This may hold true for transurethral prostate ablation and/or sonication hyperthermia, which is thus the application most likely to benefit from these insights.

Embodiments of the invention may be applicable to transurethral HIFU ablation. Transrectal prostate ablation may also benefit as may interstitial catheter based HIFU applications. Applications where hyperthermia is induced by sonication may benefit just as much as ablation applications. HIFU ablation is used to kill tissue directly by heating, whereas HIFU induced hyperthermia can be used to sensitize the tissue to radiation therapy, for local drug delivery and for local gene therapy and/or expression for example.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 102 array of capacitive micromachined ultrasound transducers
104 array of capacitive micromachined ultrasound transducers
108 first electrical connection
110 second electrical connection
112 blowup view of array 102
114 capacitive micromachined ultrasound transducer
116 set of first electrical connections
118 set of second electrical connections
120 blowup view of array 104
122 capacitive micromachined ultrasound transducer
124 first electrical connection
126 second electrical connection
200 distal end of catheter
202 forward looking ring array
204 sideward looking array
205 shaft
206 electrical connection
208 hole
300 catheter
302 array of capacitive micromachined ultrasound transducers
303 flexible element
304 path of ultrasound
306 target zone
308 distal end
310 shaft
312 tube
314 cable
316 direction of cable travel
400 catheter
402 prostate
404 bladder
406 distal end
407 array of capacitive micromachined ultrasound transducers
408 mechanical actuator
410 cable
500 catheter
502 shaft
504 distal end
506 proximal end
508 array of capacitive micromachined ultrasound transducers
510 electrical connections
510' data bus and power supply
512 connector
514 target zone
600 catheter
602 processor
604 flow or pressure sensor
606 temperature sensor
608 fluid cooling inlet
610 tube
612 outlet
614 seal
900 medical instrument
902 subject
904 catheter
906 distal end
908 target zone
910 catheter interface
911 high intensity focused ultrasound system
912 computer
914 hardware interface
916 processor
918 user interface
920 computer storage
922 computer memory
924 treatment plan
926 traversal distance
928 sonication frequency
930 traversal distance calculation module
932 sonication frequency determination module
934 high intensity focused ultrasound system control module
1000 medical instrument
1001 magnetic resonance imaging system
1002 magnet
1003 bore of magnet
1004 magnetic field gradient coil
1005 imaging zone
1006 magnetic field gradient coil power supply
1008 antenna
1010 transceiver
1012 subject support
1020 pulse sequence
1021 magnetic resonance data
1022 thermal magnetic resonance data
1024 magnetic resonance image
1026 thermographic magnetic resonance image
1028 planning magnetic resonance data
1030 planning magnetic resonance image
1032 magnetic resonance imaging system control module
1034 image reconstruction module
1036 thermal mapping module
1038 treatment plan modification module
1040 image registration module
1042 ultrasound simulation model
1100 depth (mm)
1102 absorbed energy
1104 absorption as function of penetration depth for 5 MHz
1106 absorption as function of penetration depth for 10 MHz
1108 absorption as function of penetration depth for 20 MHz
1200 frequency MHz
1202 absorbed energy
1204 absorption as function of frequency at 5 mm
1206 absorption as function of frequency at 10 mm
1208 absorption as function of frequency at 20 mm

The invention claimed is:

1. A medical instrument comprising:
   a catheter; and
   a high intensity focused ultrasound system comprising an ultrasound transducer with an adjustable sonication frequency configured to ultrasound into a sonication volume, wherein the ultrasound transducer comprises a first two-dimensional array and a second two-dimensional array of capacitive micromachined transducers, the first and second two-dimensional arrays disposed at different sideways-looking angular positions around the distal end of the catheter, the first and second arrays being configured to operate independently of each other;
   a processor configured to control the medical instrument;
   a memory configured to store machine executable instructions, wherein execution of the instructions causes the processor to:

receive a treatment plan descriptive of a target zone within a subject;

determine a traversal distance through the subject to the target zone using the treatment plan, wherein the traversal distance is descriptive of a traversal of ultrasound from the ultrasound transducer to the target zone;

determine a sonication frequency using the traversal distance for focusing the sonication volume onto the target zone; and control the high intensity focused ultrasound system to sonicate the target zone to perform ultrasound ablation at the sonication frequency including performing electronic beam steering of the sonication;

wherein each of the capacitive micromachined ultrasound transducers of each of the first and second arrays has a separately controllable sonication amplitude and phase, wherein execution of the instructions causes the processor to determine the sonication frequency for each of the capacitive micromachined ultrasound transducer arrays and to perform electronic beam steering of the sonication by changing amplitude and phase for the capacitive micromachined ultrasound transducers; and wherein execution of the instructions causes the processor to determine a first sonication frequency using the traversal distance for focusing the sonication volume into the target zone, wherein execution of the instructions causes the processor to determine a second sonication frequency using the traversal distance for focusing the sonication volume into the target zone, and wherein execution of the instructions causes the processor to sonicate the target zone using the high intensity focused ultrasound system using the first sonication frequency for the first array of capacitive micromachined transducers and using the second sonication frequency for the second array of capacitive micromachined transducers.

2. The medical instrument of claim 1, wherein the medical instrument further comprises a magnetic resonance imaging system configured to acquire magnetic resonance data from an imaging zone, wherein the target zone is within the imaging zone, wherein execution of the instructions further causes the processor to repeatedly:

acquire the magnetic resonance data using the magnetic resonance imaging system;

reconstruct a magnetic resonance image; and modify the treatment plan in accordance with the magnetic resonance image.

3. The medical instrument of claim 2, wherein the magnetic resonance data comprises thermal magnetic resonance data, and wherein the magnetic resonance image is a thermographic magnetic resonance image.

4. The medical instrument of claim 2, wherein execution of the instructions further causes the processor to:

acquire planning magnetic resonance data using the magnetic resonance imaging system;

reconstruct a planning magnetic resonance image; and modify the treatment plan in accordance with the planning magnetic resonance image.

5. The medical instrument of claim 1, wherein the sonication frequency is determined using an ultrasound simulation model.

6. The medical instrument of claim 1, wherein the catheter comprises:

a shaft with the distal end and a proximal end; and a connector at the proximal end of the shaft for supplying the first capacitive micromachined ultrasound transducer array and the second capacitive micromachined ultrasound transducer array with electrical power and for controlling the first sonication frequency and the second sonication frequency.

7. The medical instrument of claim 6, wherein the first capacitive micromachined ultrasound transducer array has a first adjustable focus and the second capacitive micromachined ultrasound transducer array has a second adjustable focus, wherein the first adjustable focus is at least partially operable for being adjusted by electronic control, wherein the second adjustable focus is at least partially operates for being adjusted by electronic control, and wherein the sonication volume is a superposition of the first adjustable focus and the second adjustable focus.

8. The medical instrument of claim 7, wherein the distal end of the catheter comprises at least one integrated circuit configured to power the first capacitive micromachined ultrasound transducer array and the second capacitive micromachined ultrasound transducer array and configured to provide electronic control of the first capacitive micromachined ultrasound transducer array and the second capacitive micromachined ultrasound transducer array, and wherein the catheter further comprises a data bus between the at least one integrated circuit and the connector.

9. The medical instrument of claim 1 wherein the first sonication frequency and the second sonication frequency are not harmonics or identical.

10. The medical instrument of claim 1 further comprising:

a forward-facing array of capacitive micromachined ultrasound transducers disposed at a tip of the distal end of the catheter, the forward-facing array being configured to perform ultrasound imaging.

11. A medical instrument comprising:

a high intensity focused ultrasound system comprising an ultrasound transducer with an adjustable sonication frequency configured to focus ultrasound into a sonication volume, wherein the ultrasound transducer comprises at least first and second arrays of capacitive micromachined transducers;

a catheter, the first and second arrays of capacitive micromachined transducers being sideways-looking arrays disposed on a side of a distal end of the catheter;

a forward-facing array of capacitive micromachined ultrasound transducers disposed at a tip of the distal end of the catheter, the forward-facing array of capacitive micromachined ultrasound transducers being configured to perform ultrasound imaging;

a processor configured to control the medical instrument;

a memory configured to store machine executable instructions, wherein execution of the instructions causes the processor to:

receive a treatment plan descriptive of a target zone within a subject;

determine a traversal distance through the subject to the target zone using the treatment plan, wherein the traversal distance is descriptive of a traversal of ultrasound from the ultrasound transducer to the target zone;

determine a first sonication frequency for the first array of capacitive micromachined transducers using the traversal distance for focusing the sonication volume onto the target zone;

determine a second sonication frequency for the second array of capacitive micromachined transducers using the traversal distance for focusing the sonication volume onto the target zone; and control the first and second arrays of the high intensity focused ultrasound system to sonicate the target zone at the respective first and second sonication frequencies including performing electronic beam steering of the sonication by changing amplitude and phase for the capacitive micromachined ultrasound transducers;

wherein each of the capacitive micromachined ultrasound transducers of each of the first and second arrays has a separately controllable sonication amplitude and phase, wherein execution of the instructions causes the processor to determine the sonication amplitude and phase for each of the capacitive micromachined ultrasound transducers of the first and second arrays of capacitive micromachined transducers.

12. A medical instrument comprising:

a high intensity focused ultrasound system comprising an ultrasound transducer with an adjustable sonication frequency configured to focus ultrasound into a sonication volume;

a catheter, wherein the high intensity focused ultrasound system includes a plurality of arrays of capacitive micromachined transducers each comprising an instance of the array of the capacitive micromachined transducers arranged as sideways-looking arrays around a distal end of the catheter whereby the medical instrument is configured to sonicate a target zone 360 degrees around the distal end of the catheter without mechanical rotation;

a processor configured to control the medical instrument;

a memory configured to store machine executable instructions, wherein execution of the instructions causes the processor to:

receive a treatment plan descriptive of the target zone within a subject;

determine a traversal distance through the subject to the target zone using the treatment plan, wherein the traversal distance is descriptive of a traversal of ultrasound from the ultrasound transducer to the target zone;

determine a first sonication frequency for a first array of capacitive micromachined transducers of the plurality of arrays of capacitive micromachined transducers using the traversal distance for focusing the sonication volume onto the target zone;

determine a second sonication frequency for a second array of capacitive micromachined transducers of the plurality of arrays of capacitive micromachined transducers using the traversal distance for focusing the sonication volume onto the target zone; and control the arrays of the high intensity focused ultrasound system to sonicate the target zone at the respective first and second sonication frequencies including performing electronic beam steering of the sonication by changing amplitude and phase for the capacitive micromachined ultrasound transducers;

wherein each of the capacitive micromachined ultrasound transducers of each of the first and second arrays has a separately controllable sonication amplitude and phase, wherein execution of the instructions causes the processor to determine the sonication amplitude and phase for each of the capacitive micromachined ultrasound transducers of the first and second arrays of capacitive micromachined transducers.

* * * * *